United States Patent

Unger

[11] Patent Number: 5,842,864
[45] Date of Patent: Dec. 1, 1998

[54] PROSTHETIC SUPERSTRUCTURE

[76] Inventor: Heinz-Dieter Unger, Kommenderiestrasse 124, D-49080 Osnabruek, Germany

[21] Appl. No.: 849,587
[22] PCT Filed: Dec. 1, 1995
[86] PCT No.: PCT/EP95/04733
    § 371 Date: Jun. 3, 1997
    § 102(e) Date: Jun. 3, 1997
[87] PCT Pub. No.: WO96/17560
    PCT Pub. Date: Jun. 13, 1996

[30] Foreign Application Priority Data

Dec. 6, 1994 [DE] Germany ............ G 94 19 508.0

[51] Int. Cl.$^6$ .................................................. A61C 13/12
[52] U.S. Cl. .............................. 433/172; 433/182
[58] Field of Search ......................... 433/172, 173, 433/181, 182

[56] References Cited

U.S. PATENT DOCUMENTS

| | | | |
|---|---|---|---|
| 2,599,044 | 6/1952 | Brennan | 433/173 |
| 3,672,057 | 6/1972 | Mays | 433/172 |
| 5,106,299 | 4/1992 | Ghalili | 433/172 |
| 5,133,662 | 7/1992 | Metcalfe | 433/173 |

Primary Examiner—John J. Wilson
Attorney, Agent, or Firm—Jordan and Hamburg

[57] ABSTRACT

A prosthetic superstructure has a locking device, which can be placed on a spherical head or on a similar connecting part of an implant and fixed to this and which can be accommodated in a dental prosthesis. The locking device includes locking parts, which can be moved by means of an adjusting element into and out of a locking engagement with the spherical head of the implant and the end of the adjusting element, can be actuated by means of an artificial tooth, which is disposed in the dental prosthesis close to the locking device.

21 Claims, 4 Drawing Sheets

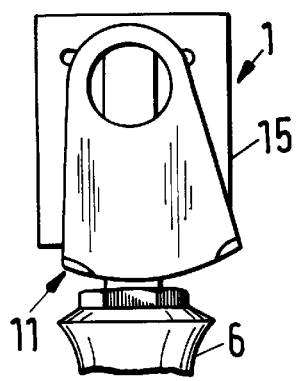
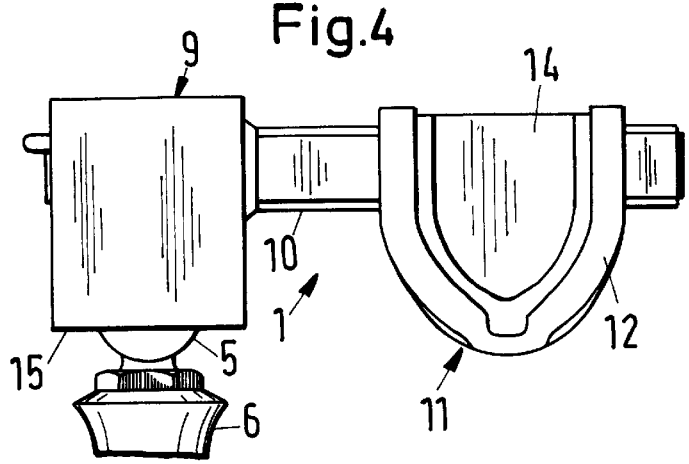
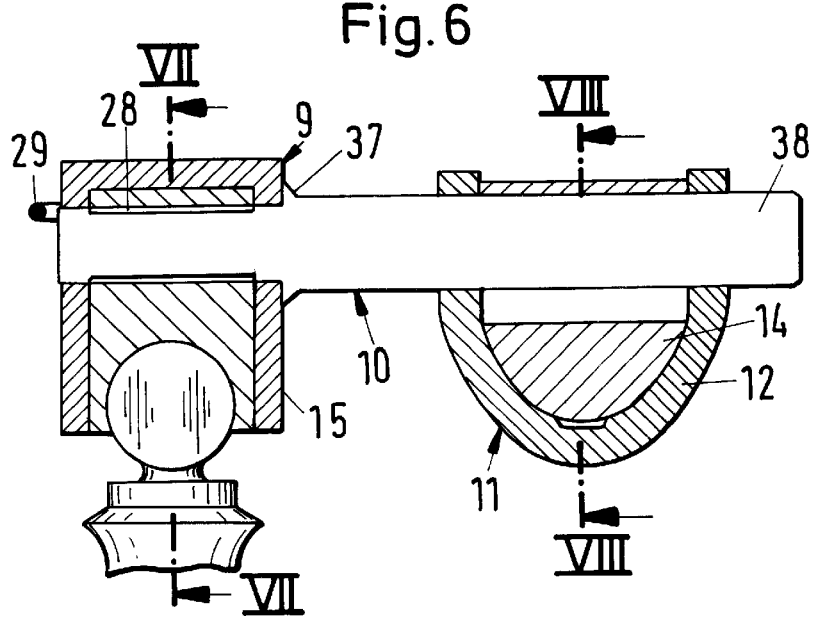
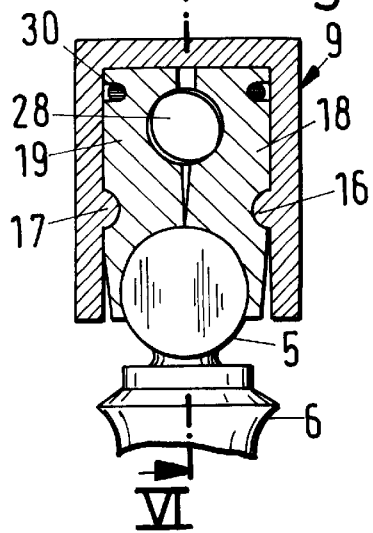
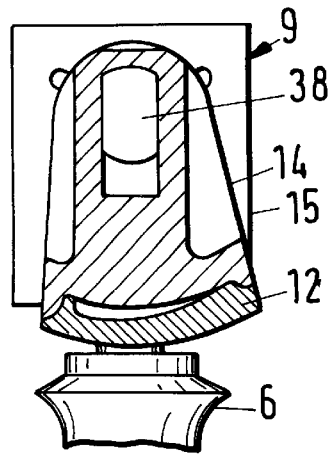

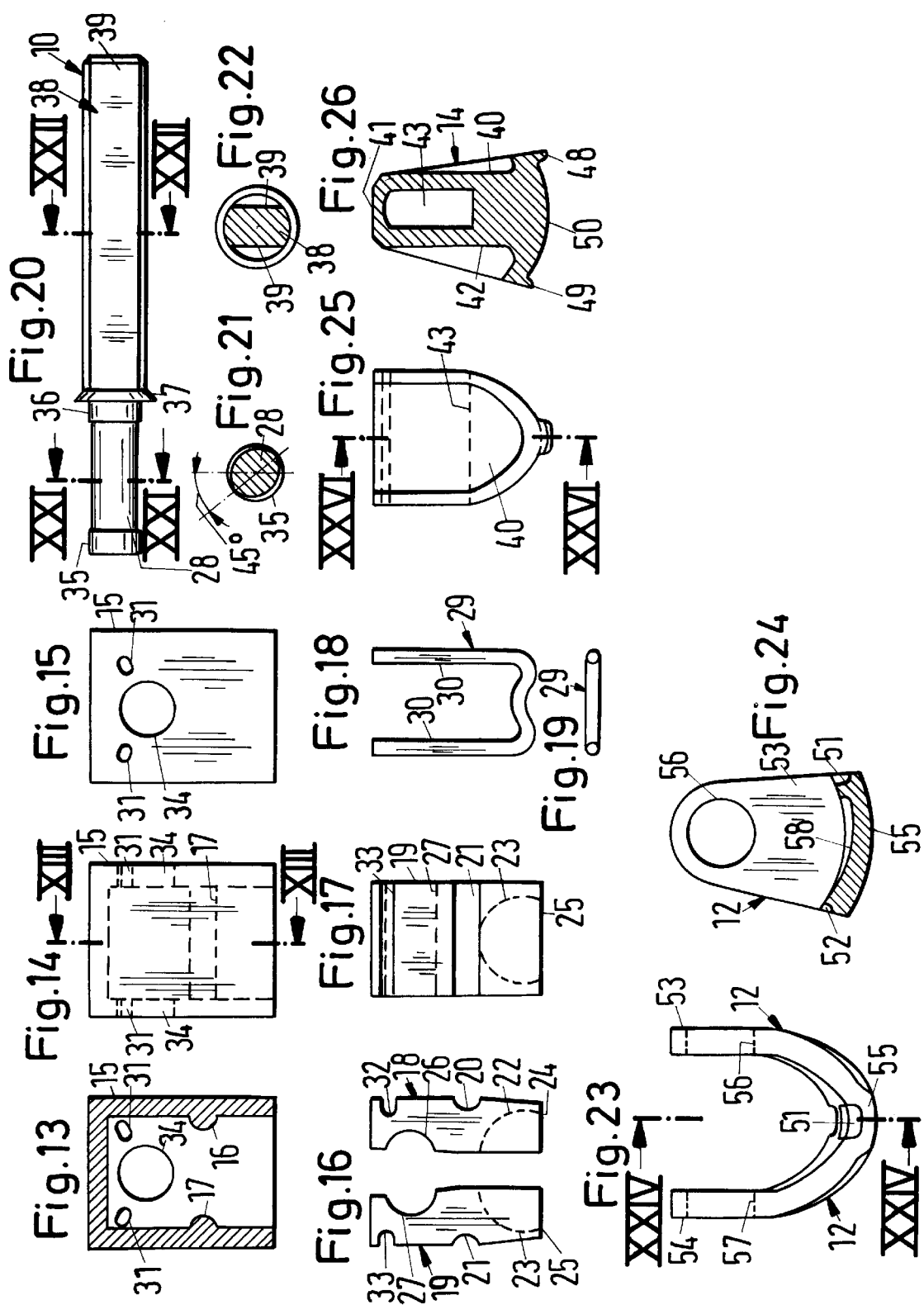

PROSTHETIC SUPERSTRUCTURE

BACKGROUND OF THE INVENTION

The invention relates to a prosthetic superstructure.

In the case of a known superstructure of this type, the locking device is based on a snap fastener system. Such a superstructure imposes relatively high, largely uncontrolled tensile forces which jeopardize the satisfactory seating of the implant on the implant during removal of the dental prosthesis. A different, known superstructure makes use of the swiveling locking bar technique for which a swiveling locking bar can be swiveled into and out of engagement with a locking recess in the implant in order to bring about or to terminate the connection between the dental prosthesis and the connecting part of the implant. Such a superstructure admittedly does not exert any pull-off forces on the implant. However, as a laboratory-manufactured construction, it is relatively expensive and requires an appreciable number of fitting dates. The primary part of the locking device, moreover, can be the cause of hygienic problems in the mouth and even of inflammations of the mucous membrane, while the secondary part forms an interfering factor for the tongue and mucous membranes, since it forms an inwardly protruding, somewhat sharp-edged part.

SUMMARY OF THE INVENTION

It is an object of the invention to provide a superstructure, which is constructed simply and handled easily, is comfortable to wear and does not exert any pull-off forces on the implant.

The inventive superstructure can be produced cost-effectively industrially, does not exert any forces on the implant when put on or taken off and can be looked after easily by the wearer. It is very comfortable to wear, since it is embedded completely in the prosthesis construction and avoids protruding parts, and cannot be identified visually, since all parts are accommodated so as to be hidden. The inventive superstructure furthermore is wear-free and does not require any post-activation. It can be taken care of effectively with simple means and produces a compensatory effect when pushed in from different directions. Finally, it can be handled easily by the dental technician and the person being treated and exchanged without any problems and requires only a few sessions from the start to the end of the treatment.

Numerous further details and advantages arise out of the following description and the drawing, in which a preferred object of the invention is illustrated in greater detail.

IN THE DRAWINGS

FIG. 1 shows a sectional representation of a vertical, longitudinal section through an inventive superstructure, which is disposed in a dental prosthesis and fixed on an implant, FIG. 2 shows a section along the line II—II of FIG. 1, FIG. 3 shows a section along the line III—III of FIG. 1, FIG. 4 shows a detailed representation of the superstructure in front view, FIG. 5 shows a view of the right end face of the superstructure in FIG. 4, FIG. 6 shows a section along the line VI—VI in FIG. 7, FIG. 7 shows a section along the line VII—VII in FIG. 6, FIG. 8 shows a section along the line VIII—VIII in FIG. 6, FIG. 9 shows a sectional representation of the guiding and locking device for the tooth forming the actuator, FIG. 10 shows a section along the line X—X in FIG. 9, FIG. 11 shows a modified embodiment similar to that of FIG. 9, FIG. 12 shows a section along the line XII—XII in FIG. 11, FIG. 13 shows a section through the housing of the locking device along the line XIII—XIII of FIG. 14, FIG. 14 shows a front view of the housing of the locking device, FIG. 15 shows a side view of the housing of the locking device, FIG. 16 shows a side view of the locking jaws, FIG. 17 shows a front view of the locking jaw, FIG. 18 shows a plan view of the spring for pretensioning the locking jaw, FIG. 19 is an end view to FIG. 18, FIG. 20 shows a side view of the adjusting shaft, FIG. 21 shows a section along the line XXI—XXI of FIG. 20, FIG. 22 shows a section along the line XXII—XXII of FIG. 20, FIG. 23 shows a front view of the abutment of the guiding and locking device, FIG. 24 shows a side view of FIG. 23, FIG. 25 shows a front view of the swiveling carrier of the guiding and locking device, and FIG. 26 is a section taken along the line XXVI—XXVI in FIG. 25.

DESCRIPTION OF THE PREFERRED EMBODIMENTS

Figure 1:
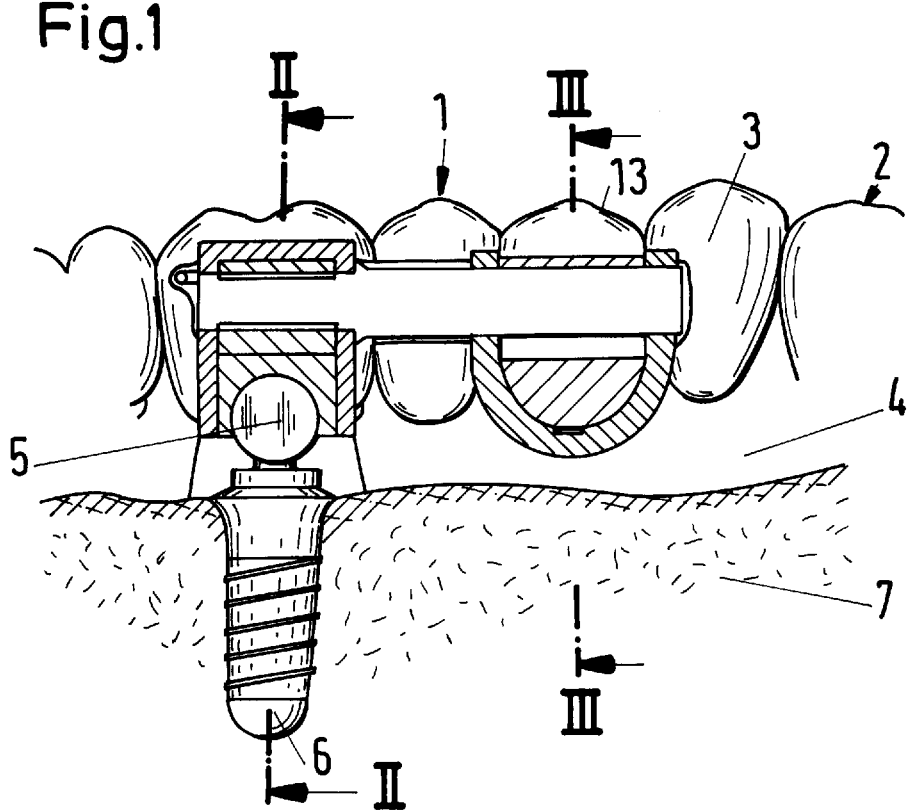
Figure 2:
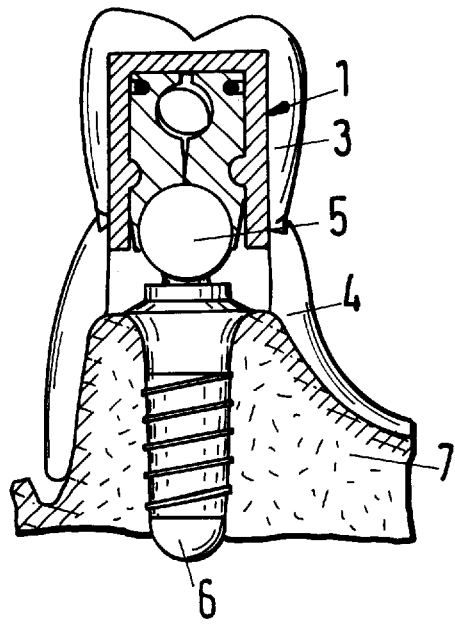
Figure 3:
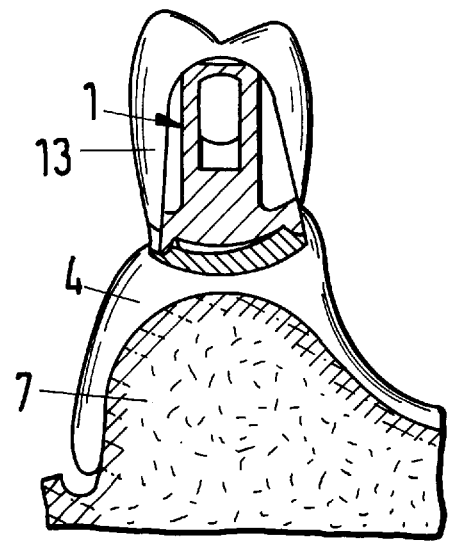

FIGS. 1 to 3 illustrate, in sectional representations, the superstructure 1 of the inventive construction, installed in an stalling position in a dental prosthesis 2 with teeth 3 and prosthesis saddle 4. The superstructure 1 is fixed on the spherical head 5 of an implant 6, which is implanted in a jawbone 7.

Basically, the superstructure 1 can be used for any type of dental prosthesis or denture and is suitable for lower jaw prostheses as well as for upper jaw prostheses. The number of superstructures 1, used per dental prosthesis, can be varied depending on circumstances.

As can be seen in greater detail in the enlarged representation of the inventive superstructure 1 in FIGS. 4 to 12, the superstructure 1, in detail, comprises a locking device 9, an adjusting element 10 in the form of an adjusting shaft and a guiding and locking device 11, which consists of an abutment 12 and a swivel carrier 14 for a tooth 13, forming the actuator of the adjusting element 10.

In detail, the locking device 9, comprises a housing 15, which is open at the jaw side and, at the inside of its front and rear side walls of the locking device 9, has a bearing shoulder 16, 17 in the form of a cylindrical segment. Furthermore, the locking device 9 comprises two locking jaws 18, 19, which have the same construction and are supported in the housing 15, so that they can pivot in opposite directions to a limited extent. For this purpose, the locking jaws 18, 19 have at their outside a bearing recess 20, 21, which is disposed approximately centrally, has the shape of a cylindrical segment and extends over the whole width of the jaws. At the bearing recess 20, 21, the locking jaws 18, 19, when they are in the installing position, in each case engage a bearing shoulder 16 or 17.

Internally, the locking jaws have a partially spherical recess 22, 23, which conforms with the surface of the spherical head 5 of the implant 6 and the lower edge 24, 25 of which, when engaging the spherical head 5, overlaps the center plane of the spherical head 5. When in the position, in which they engage the spherical head 5, the locking jaws 18, 19 therefore ensure that the superstructure 1 is seated firmly.

At their interior sides facing one another in the installing position, the locking jaws 18, 19 are provided with recesses 26, 27, which are in the form of a cylindrical segment and form the boundary of an adjusting space, into which the adjusting shaft 10 reaches with a cam part 28. The latter is constructed elliptically in cross section and forms a spreader which, when engaging the recesses 26, 27 of the locking jaws 18, 19, imparts a swiveling motion about the bearing shoulder 16, 17 at the housing 15. As a result of this swiveling motion, the locking jaws 18, 19, with their recesses 22, 23, attain a locking engagement on the spherical head 5 of the implant 6. The main axis of the elliptical contour of the cam part 28 is inclined at an angle of 45° to the vertical in the locking position and is aligned vertically in the unlocking position of the cam part 28. The bearing shoulders 16, 17 define the swiveling axes of the locking jaws 18, 19, which are aligned parallel to the center line of the adjusting shaft 10 and placed at a distance below the cam part 28.

In the installing position, the locking jaws 18, 19 are acted upon by a spring 29, which endeavors to pull the locking jaws 18, 19 into their unlocked position, in which they do not engage the spherical head 5 of the implant 6. The spring 29 consists of a U-shaped wire spring body, the longitudinal legs 30 of which pass through elongated openings 31 in the side walls of the housing 15, extending perpendicular to the bearing shoulders 16, 17, as well as through recesses 32, 33 in the outer sides of the locking jaws 18, 19, when they are in the installing position.

In the same side walls, in which the openings 31 are located, there are openings 34, which are aligned with one another and serve to supportively accommodate cylindrical bearing regions 35, 36 of the adjusting shaft 10. The adjusting shaft 10, where it adjoins the interior bearing region 36, is provided with a collar 37 which, in the installing position, lies against the outside of the housing 15 facing the guiding and locking device 11 and, in this manner, positions the adjusting shaft 10 in the axial direction. The region 38 of the adjusting shaft 10, adjoining the collar 37, is provided at parallel, opposite sides with a flattening 39, which forms guiding surfaces for the swiveling carrier 14 of the guiding and locking device 11.

Figure 9:
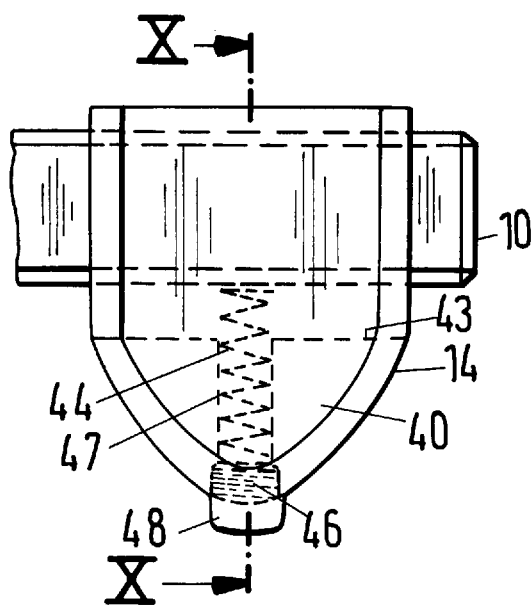
Figure 10:
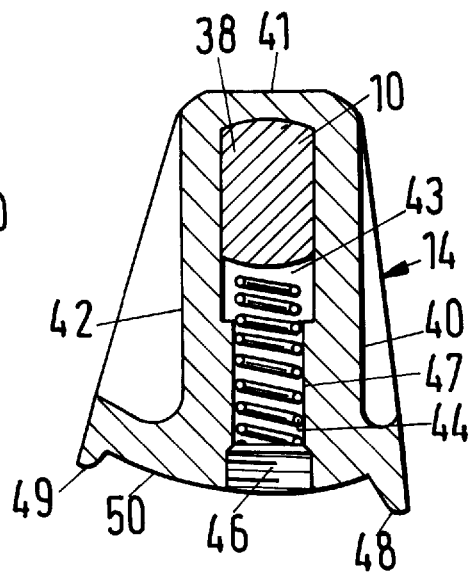
Figure 11:
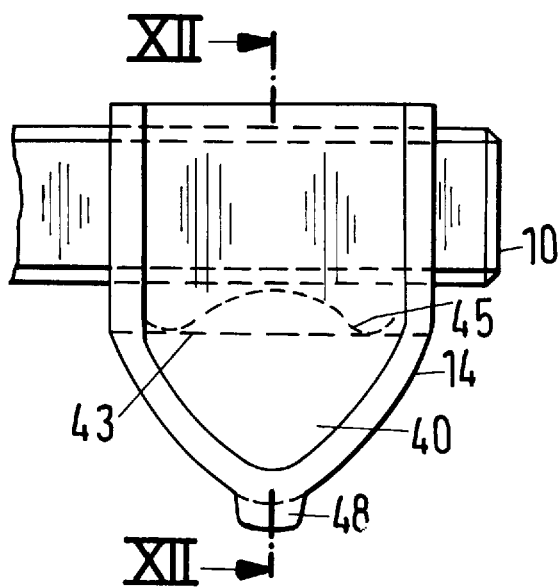
Figure 12:
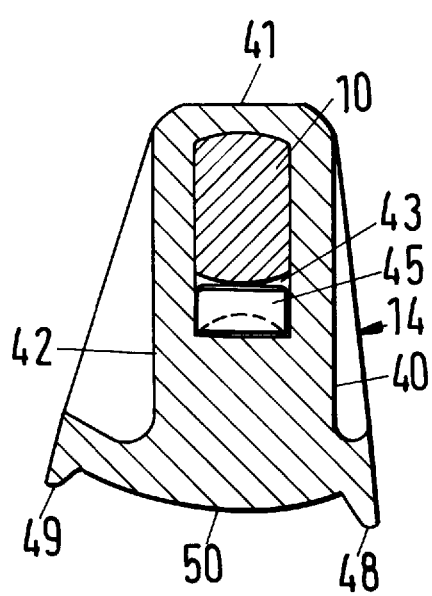

At the front, top and rear, the swiveling carrier 14 has mounting surfaces 40, 41 and 42 for affixing an artificial tooth 13 and comprises a recess 43 for accommodating the flattened region 38 of the adjusting shaft 10, which is matched closely to the contour of the flattened region 38 of the shaft 10 but, in the direction parallel to the flattenings 39, has dimensions, which exceeds the dimensions of the flattened region 38 of the shaft 10 specified in the same direction. Accordingly, the swiveling carrier 14 can be shifted to a limited extent radially with respect to the adjusting shaft 10. In the swiveling carrier 14, a spring is supported on one side at the adjusting shaft 10 and endeavors to press the swiveling carrier 14 into a basic position relative to the adjusting shaft 10. In the construction of FIGS. 9 and 10, this spring is formed as a spiral spring 44, which is accommodated in a borehole 47 that is closed off by a screw 46. In the construction of FIGS. 11 and 12, the spring is formed as a leaf spring 45, which is accommodated in the recess 43 and fixed there.

Adjoining its front and rear side, the swiveling carrier 14 is provided with locking shoulders 48, 49, which protrude towards the abutment 12 of the guiding and locking device 11 and between which the arc-shaped underside 50 of the swiveling carrier 14 extends. In the basic position of the swiveling carrier 14, the locking shoulders 48, 49 mesh with the locking recesses 51, 52, which are provided in the swiveling carrier 14, adjoining the front and rear sides of the abutment 12.

The abutment 12 is forked and has forked legs 53, 54 and a forked bottom 55. The forked legs 53, 54 are provided with mutually aligned bearing openings 56, 57. The adjusting shaft 10 is passed through and supported in these bearing openings 56, 57, in which, in the installing position, it is accommodated with its flattened shaft region 38. In the installing position, the forked legs 53, 54 are embedded in the two teeth 3 of the dental prosthesis 2, which are adjacent on either side of the tooth 13 forming the actuator. The forked bottom 55 is embedded in the prosthesis saddle 4. At its upper side, the forked bottom 55 has a path 55, which is curved arc-shaped and forms a gravity incline.

As can be inferred from FIGS. 1 and 3, as well as 6 and 8, the fork-shaped abutment 12 surrounds the swivel carrier 14 at the sides and underneath in the installing position in the dental prosthesis, the locking shoulders 48 and 49 engaging the locking recesses 51 and 52 respectively in the basic position. In this basic position, the adjusting shaft 10 and its cam part 28 assume a position, in which they are at an angle of 45° to the vertical and in which the cam part 28 has transferred the locking jaws 18, 19 together with the head 5 of the implant 6 into the locking engagement. To remove the dental prosthesis 2, the tooth 13, concealing the swivel carrier 14, is lifted a little, until the locking shoulder 49 is lifted out of the locking recess 52. In this release position, the swivel carrier 14 is now swiveled clockwise together with its tooth 13 in FIGS. 3 and 8, until the locking shoulder 49 reaches the end of the path 58. For this purpose, a slight swiveling motion suffices at first, by means of which the locking shoulder 49 reaches the forked bottom 55 of the abutment 58 by way of the path 58, after which the locking shoulder 49 can be placed on the path 58, before the swiveling motion is continued. The locking shoulder 48 is longer than the locking shoulder 49 so that, after the swivel carrier 14 is lifted off completely, the latter can be swiveled only in the clockwise direction.

In the course of the swiveling motion, as soon as the locking shoulder 49 has reached the end of the path 58, the locking jaws 18, 19 of the locking device 9 are in the unlocking position, so that the dental prosthesis 2 can be lifted off without any pull-off forces. In this position of the parts, the dental prosthesis can be cleaned without difficulty and the dental prosthesis then set down free of compressive forces. At the same time, the superstructure 1 can be fixed once again on the implant 6 associated with it. For this purpose, it suffices to raise the swivel carrier 14 with its tooth 13 slightly and to swivel it back subsequently into the basic position, in which the locking engagement of the locking jaws 18, 19 with the spherical head 5 can be brought about once again by the cam part 28. After the locking shoulders 48, 49 are engaged in the locking recesses 51, 52, a secure seat of the dental prosthesis 2 is ensured, the superstructure being accommodated completely invisibly.

In the case of the preferred embodiment shown, the adjusting shaft is constructed in one piece. However, the possibility also exists of forming, for example, the part of the adjusting shaft 10, which is to the left of collar 37 in FIG. 6, as a separate part and, with a shoulder part in the flattened part to the right of the collar 37 in FIG. 6, of supporting it so that it can be swiveled to a limited extent about the center line of the adjusting shaft and, at the same time, of pretensioning it by a torsion spring for a movement into that end position, which the cam part 28 is to assume on the spherical head 5 in the locking position of the locking jaws 18, 19. By these means, the possibility is created of acting upon the locking jaws 18, 19 by the cam part 28 of the adjusting shaft 10 in the locking sense with a force, which arises out of the pretensioning of the cam part 28 by the torsion spring. This avoids any overloading, provides a self adjustment and eliminates the need for a very precise angular coordination of the parts with one another, a coordination which, in the basic position of the swivel carrier 14, specifies the final locking position for the locking jaws 18, 19.

I claim:

1. A prosthetic superstructure for use with a dental prosthesis, said superstructure comprising a locking device accommodated in said dental prosthesis and adapted to be secured to a connecting part of an implant, said locking device comprising locking parts movable into a locking position in locking relationship with said connecting part and an unlocking position out of locking relationship with said connecting part, and adjustment device for moving said locking device into said locking and said unlocking positions, and an actuating device disposed in a false tooth on the dental prosthesis for actuating said adjustment device, said false tooth in which said actuating device is disposed being movable between a first position and a second position, said false tooth in moving between said first and second positions effecting movement of said actuating device between an engaged and a release position independently of said adjustment means.

2. A prosthetic superstructure according to claim 1 wherein said false tooth is moveable between said second position and a third position, said false tooth in moving from said second position to said third position effecting movement of said actuating device from said release position to an actuated position, said movement of said actuating device from said release position to said actuated position effecting movement of said adjustment device from said locking position to said unlocking position.

3. A prosthetic superstructure according to claim 1 wherein said actuating device includes a biasing means between said actuating device and said adjustment device for biasing said actuating device toward said engaged position.

4. A prosthetic superstructure according to claim 1 wherein said false tooth in which said actuating device is installed has a saddle, said actuating device including an actuator locking means which locks said actuating device to said saddle when said actuating device is in said engaged position.

5. A prosthetic superstructure according to claim 1 wherein said adjustment device includes a shaft having a longitudinal axis, said actuating device in moving from said engaged position to said release position moving in a direction transversely of said longitudinal axis.

6. A prosthetic superstructure for use with a dental prosthesis, said superstructure comprising a locking device accommodated in said dental prosthesis and adapted to be secured to a connecting part of an implant, said locking device comprising locking parts movable into a locking position in locking relationship with said connecting part and an unlocking position out of locking relationship with said connecting part, an adjustment device for moving said locking device into said locking and said unlocking positions, and an actuating device disposed in a false tooth on the dental prosthesis for actuating said adjustment device, said locking device being accommodated in a first false tooth of the dental prosthesis, said adjustment device comprising a shaft which passes through a second false tooth of said dental prosthesis, said second tooth being juxtaposed to said first false tooth, said false tooth in which said actuating device is accommodated being juxtaposed to said second false tooth.

7. A prosthetic superstructure for use with a dental prosthesis, said superstructure comprising a locking device accommodated in said dental prosthesis and adapted to be secured to a connecting part of an implant, said locking device comprising two locking parts movable into a locking position in locking relationship with said connecting part and an unlocking position out of locking relationship with said connecting part, said two locking parts having juxtaposed sides each having juxtaposed generally semi-circular recesses which together form a generally cylindrical recess when said two locking parts are in their locking position, an adjustment device for moving said locking device into said locking and said unlocking positions, said adjustment device including an adjustment shaft having a cam section extending into said generally cylindrical recess, and an actuating device disposed in a false tooth on the dental prosthesis for actuating said adjustment device.

8. A prosthetic superstructure for use with a dental prosthesis, said superstructure comprising a locking device accommodated in said dental prosthesis and adapted to be secured to a connecting part of an implant, said locking device comprising two locking parts movable into a locking position in locking relationship with said connecting part and an unlocking position out of locking relationship with said connecting part, said locking device comprising a housing having an opening, said locking device further comprising pivot means for pivotably supporting said two locking parts in said housing for pivotal movement in opposite directions between said locking position and said unlocking position, said two locking parts each having a cam portion, an adjustment device for moving said locking device into said locking and said unlocking positions, said adjustment device including an adjusting shaft mounted on said housing and having a cam section engageable with said cam portion of said two locking parts, whereby rotation of said adjusting shaft effects movement of said two locking parts between said locking and said unlocking position, and an actuating device disposed in a false tooth on the dental prosthesis for actuating said adjustment device.

9. A prosthetic superstructure according to claim 8 wherein said adjusting shaft has a longitudinal axis, said pivot means comprising pivotal supports on said housing for pivotably supporting said two locking parts for pivotal movement about pivotal axes parallel to the longitudinal axis of said adjusting shaft, said pivotal axes of said pivotal supports being spaced from said longitudinal axis of said adjusting shaft.

10. A prosthetic superstructure according to claim 8 wherein said locking device comprises biasing means biasing said two locking parts toward their unlocking position.

11. A prosthetic superstructure according to claim 10 wherein said biasing means includes a U-shaped spring having longitudinal legs, said housing having openings through which said legs extend, said two locking parts having recesses which accommodate said legs, said pivot means pivotably supporting said two locking parts for pivotal movement about two parallel pivot axes, said legs being generally parallel to said pivotal axes of said two locking parts.

12. A prosthetic superstructure according to claim 8 wherein said housing has side walls having aligned openings, said adjusting shaft being rotatably mounted in said aligned openings, said adjusting shaft having a cam section between said two openings, said cam section having an approximately elliptical cross sectional configuration.

13. A prosthetic superstructure according to claim 12 wherein said adjusting shaft has a collar disposed against the outside of one of said side walls of said housing, said collar being located between said one side wall and said actuating device.

14. A prosthetic superstructure according to claims 13 wherein said adjusting shaft has a flat-sided section which extends from said collar to said actuating device, said shaft having a longitudinal axis, said flat-sided section having opposed flat sides parallel to said longitudinal axis.

15. A prosthetic superstructure for use with a dental prosthesis, said superstructure comprising a locking device accommodated in said dental prosthesis and adapted to be secured to a connecting part of an implant, said locking device comprising two locking parts movable into a locking position in locking relationship with said connecting part and an unlocking position out of locking relationship with said connecting part, said locking device including a housing and pivotal supports on said housing and on said two locking parts for pivotally supporting said locking parts on said housing for movement between said locking and said unlocking position, said pivotal supports including recesses in said locking parts, said recesses having the configuration of a partial cylinder which extends over the width of the locking parts, said housing having projections having the configuration of a partial cylinder corresponding to the partial cylindrical configuration of said recesses such that said recesses receive said projections to provide a pivotal relationship therebetween, an adjustment device for moving said locking device into said locking and said unlocking positions, and an actuating device disposed in a false tooth on the dental prosthesis for actuating said adjustment device.

16. A prosthetic superstructure for use with a dental prosthesis, said superstructure comprising a locking device accommodated in said dental prosthesis and adapted to be secured to a connecting part of an implant, said locking device comprising locking parts movable into a locking position in locking relationship with said connecting part and an unlocking position out of locking relationship with said connecting part, an adjustment device for moving said locking device into said locking and said unlocking positions, and an actuating device disposed in a false tooth on the dental prosthesis for actuating said adjustment device, said actuating device including a fork-shaped abutment member and a carrier moveable relative to said fork-shaped abutment member.

17. A prosthetic superstructure according to claim 16 wherein said fork-shaped abutment member is disposed in said false tooth in which said actuating device is installed, the last said false tooth being designated a first false tooth, said fork-shaped abutment member including two forked legs each having aligned bearing openings, said adjustment device including an adjusting shaft, said bearing openings receiving said adjusting shaft, said forked legs being embedded in second and third false teeth on opposite sides of said first false tooth, said fork-shaped abutment member including a connecting part connecting said two forked legs, said dental prosthesis having a saddle underlying said connecting part, said connecting part being embedded in said saddle.

18. A prosthetic superstructure according to claim 17 wherein said carrier has a recess, said adjustment shaft having a flat-sided section having two flat parallel sides, said flat-sided section of said shaft extending into said recess, said recess having two opposed generally flat parallel sides which generally conform to the opposed generally flat parallel sides on said flat-sided section of said shaft, the distance between the two flat sides on the recess being greater than the distance between the two flat sides on the flat-sided section of said shaft.

19. A prosthetic superstructure according to claim 18 wherein said actuating device includes biasing means between said carrier and said flat-sided section of said shaft for biasing said carrier toward said engaged position.

20. A prosthetic superstructure according to claim 17 wherein said connecting part has locking recesses, said carrier having locking shoulders which protrude toward said connecting part, said locking shoulders engaging said locking recesses when said actuating means is in said engaged position.

21. A prosthetic superstructure for use with a dental prosthesis, said superstructure comprising a locking device accommodated in a first false tooth of said dental prosthesis and adapted to be secured to an anchoring part in the mouth of the person on which the dental prosthesis is used, said locking device comprising locking parts movable into a locking position in locking relationship with said anchoring part and an unlocking position out of locking relationship with said anchoring part, and an actuating device disposed in a second false tooth on the dental prosthesis, said actuating device having an operable relationship with said locking means for effecting actuation of said locking device between said locking position and said unlocking position.

\* \* \* \* \*